United States Patent [19]
Sakurai et al.

[11] Patent Number: 6,083,754
[45] Date of Patent: Jul. 4, 2000

[54] METHOD OF AND APPARATUS FOR ANALYZING A PLURALITY OF COMPONENTS SIMULTANEOUSLY THROUGH CONTINUOUS FLOW ANALYSIS

[75] Inventors: Hiroyuki Sakurai; Yutaka Hayashibe; Minoru Takeya; Yasumasa Sayama, all of Omiya, Japan

[73] Assignee: Mitsubishi Materials Corporation, Tokyo, Japan

[21] Appl. No.: 08/954,201

[22] Filed: Oct. 20, 1997

[30] Foreign Application Priority Data

Oct. 24, 1996 [JP] Japan ................................ 8-282323

[51] Int. Cl.$^7$ ................................................. G01N 35/08
[52] U.S. Cl. ......................... 436/52; 422/81; 422/82.05; 422/82.09; 436/84; 436/103; 436/164
[58] Field of Search ................... 436/52, 53, 84, 436/103, 164; 422/81, 82, 82.05, 82.09

[56] References Cited

U.S. PATENT DOCUMENTS 5,114,551  5/1992  Hjerten et al. .

OTHER PUBLICATIONS

Liu et al., Talanta, vol. 40, No. 4, pp. 511–514, 1993.
Meeussen et al., Analyst, vol. 114, pp. 959–963, Aug. 1989.
Arruda et al., Analytica Chimica Acta, v. 283, pp. 476–480, 1993.
Chemical Abstracts CA100:202597. Fernandez et al., Anal. Chem., vol. 56, No. 7, pp. 1146–1151, 1984.
Chemical Abstracts CA112:245281. Mueller et al., Anal. Chim. Acta, vol. 230, No. 1, pp. 113–123, 1990.
Chemical Abstracts CA116:50476. Oguma et al., Fresenius' J. Anal. Chem., vol. 341, No. 9, pp545–9, 1991.
Chemical Abstracts CA109:243202. Hauser et al., Analyst (London), vol. 113, No. 10, pp. 1551–1555, 1988.
Chemical Abstracts CA102:124734. Baba et al., J. Chromatogr., vol. 318, No. 2, pp. 319–324, 1985.
Chemical Abstracts CA117:107598. Kang et al., Anal. Chim. Acta, vol. 261, No. 1–2, pp. 197–203, 1992.
Chemical Abstracts CA123:73700. Zolotov et al., Anal. Chim. Acta, vol. 308, No. 1–3, pp. 386–396, 1995.

*Primary Examiner*—Jan Ludlow
*Attorney, Agent, or Firm*—Oblon, Spivak, McClelland, Maier & Neustadt, P.C.

[57] ABSTRACT

A method of continuous flow analysis is provided which enables a plurality of color-forming components contained in a sample to be simultaneously analyzed with utmost ease. The method involves irradiating the sample with a measuring light which generates a wavelength having absorption bands with respect to such color-forming components, measuring the absorbance of each of the components in a color-formed state while the components are being adjusted stepwise in their color-forming state, and comparing the resultant absorbances of the components with each other. Preferably, a plurality of measuring cells are used to stepwise adjust the sample in its color-forming state, the measuring cells being connected in tandem such that a color former and/or a masking agent are incorporated in the sample while the latter is being caused to successively flow through these cells so that the sample is adjusted in its color-forming state at each of the measuring cells and measured in respect of its absorbances.

6 Claims, 4 Drawing Sheets

FIG. 7 though a capillary tube. Furthermore, the invention is
METHOD OF AND APPARATUS FOR ANALYZING A PLURALITY OF COMPONENTS SIMULTANEOUSLY THROUGH CONTINUOUS FLOW ANALYSIS

BACKGROUND OF THE INVENTION

1. Field of the Invention

The present invention is directed to a method of analyzing a plurality of components contained in a sample or specimen simultaneously or at one time through continuous flow analysis (a method of FI analysis) in which the sample is continuously analyzed while it is being caused to flow through a capillary tube. Furthermore, the invention is directed to an apparatus for use in carrying out the above method.

2. Description of the Related Art

A method of FI analysis has heretofore been known in which components contained in a sample are identified by allowing the sample to flow through a capillary tube employing a carrier fluid, adding a reagent to the sample, and then introducing the resultant sample to an analyzing or measuring section.

For instance, it is known that such method of FI analysis is employed in measuring the concentrations of impurities entrapped in a liquid specimen, such as an electrolytic zinc fluid, wherein the specimen is incorporated with a buffer solution while running the specimen through a capillary tube and then with a reagent capable of color formation upon contact with Co and Cu ions present in the liquid specimen, followed by introduction of the resultant specimen fluid to spectrometric means so as to measure the absorbances of the fluid from which the concentrations of the Co ion and also of the Cu ion are quantitatively determined (Japanese Unexamined Patent Publication No. 4-32764).

The method of FI analysis has found application in a variety of industrial sectors since it permits not only precise analysis even in the case of a small sample, but also continuous addition of reagents to the sample and simultaneous identification of the sample while it travels through a capillary channel.

However, in the case where quantitative determination is made of a plurality of components included in one specimen, the above analytical method of a FI type commonly practiced in the art requires the wavelengths to be measured to vary with the respective components in such a manner that the wavelengths do not adversely overlap making measurement impossible. This creates a problem in that the same number of absorbance meters need to be mounted corresponding to the number of the components to be identified, or measurements need to be made with variable wavelengths, consequently inviting tedious measuring conditions and inconvenient measuring systems. As another serious drawback, varied measuring wavelength leads to deviated wavelength, thus resulting in reduced precision of the analysis.

SUMMARY OF THE INVENTION

In order to eliminate the foregoing problems of the prior art which have been encountered in using the known method of FI analysis, the present invention provides a method of analyzing in a continuously flowing manner a plurality of components contained in a sample which enables analysis to be done in a simple measuring system with utmost ease and with great precision and moreover with no need for added absorbance meters or varied measuring wavelength. The invention also provides an apparatus for performing such a method with the above noted advantages.

More specifically, the present invention in one aspect provides a method of analyzing a plurality of components contained in a sample simultaneously by means of continuous flow analysis in which reagent addition and absorbance measurement are conducted at the same time during flowing of a starting sample through a measuring channel, which method comprises: irradiating the sample with a measuring light which generates a wavelength having absorption bands with respect to a plurality of color-forming components contained in the sample; measuring the absorbance of each of the components in a color-formed state while the components are being adjusted in their color-forming state in stepwise manner; and subsequently comparing the resultant absorbances of the components with each other.

In another aspect, the invention provides an apparatus for analyzing a plurality of components contained in a sample simultaneously by means of continuous flow analysis, which apparatus comprises: a measuring channel in which a sample inlet, a reagent addition pipe, a reaction tube and an absorbance meter are held in integrally communicated relation to one another; and a plurality of measuring cells mounted on the spectrophotometer, the measuring cells being connected in tandem so as to maintain therebetween a predetermined passageway with which is coupled a passage arranged to add a color former and/or a masking agent, the absorbance of a starting sample being measured every time the sample is caused to flow through each of the measuring cells.

DESCRIPTION OF THE PREFERRED EMBODIMENTS

In accordance with the present invention, (1) there is provided a method of simultaneously analyzing a plurality of components in the same sample by means of continuous flow analysis in which reagent addition and absorbance measurement are conducted at the same time during flowing of a starting sample through a measuring channel, which method comprises: irradiating the sample with a measuring absorption band to match a plurality of color-forming components present in the sample; measuring the absorbance components of each of the components in a color-formed state while the components are being adjusted in their color-forming states in stepwise manner; and subsequently comparing the resultant absorbances of the components with each other.

As light that can generate a wavelength having absorption bands with respect to a plurality of color-forming components, a light of a wavelength for example at 720 nm has absorption bands characteristic of a copper hydrate ion and a nickel hydrate ion.

Additionally, a light of a wavelength at 580 nm shows absorptions to a cobalt ion that has formed a 5-Br-PSAA (2-(5-bromo-z-pyridyllazo-5-(N-n-propyl-N-(3-sulfopuropyl)amino)-aniline sodium salt) complex and an iron ion, and a light of a wavelength at 520 nm produces absorptions to an iron ion that has formed a complex with ortho-phenanthroline and a copper ion that has formed a complex with basocuproine sulfonate. A light of a wavelength at 390 nm gives rise to absorptions in regard to a nickel hydrate ion, a thiourea complex of bismuth and a molybdic acid complex of ortho-phosphoric acid.

In another embodiment of the simultaneous analytical method according to the present invention, (2) a plurality of measuring cells are employed to adjust a sample in its color-forming state in a stepwise manner. In accordance with this embodiment, the measuring cells are connected in tandem such that a color former and/or a masking agent are incorporated in the sample while the latter is being caused to successively flow through these cells. Thus, the sample is adjusted in its color-forming state at each of the measuring cells so that the respective absorbances are measured.

The connection of the measuring cells in tandem may be made with a predetermined passageway arranged and maintained therebetween, and a passage disposed to add a color former and/or a masking agent may be communicated with such passageway. As a consequence, the sample is adjustable in its color-forming state, when desirable, at each of the measuring cells during continuous traveling of the sample through these cells.

The order required for the sample to be adjusted in its color-forming state can be decided, usually depending upon the kind of and the combination of a plurality of color-forming components contained in the sample.

For example, in the case where a sample has already been placed in a color-formed state upon preparation of the sample in liquid condition, the sample may be measured as it is in respect of its absorbance. In the case of a plurality of components having become color-formed, a masking agent of a specific composition is added to the sample so as to place either one component alone in a color-formed state, whereby the absorbance of one such component is measured. In the case of either one of a plurality of components having color-formed, a color former for use in the other component is added to bring both components into a color-formed state, whereby measurement is made of the components for their absorbances.

In the case where a sample has not yet been color-formed upon preparation of the sample in liquid condition, a colorimetric reagent solution is added to the sample so as to permit color formation of a plurality of components, whereby the latter are firstly measured in respect of their absorbances. A masking agent of a specific composition is then added to the sample, after which the absorbances of the components are measured. Alternatively, absorbance measurement is made with either one component put in a color-formed state, followed by addition of a color former for use in the other component so that both components are placed in a color-formed state and then their respective absorbances are measured.

Color formers or masking agents eligible for the present invention should have a role to convert components present in a sample into complex compounds, or otherwise vary ion bonding to thereby subject such components to color formation or protect such components from getting color-formed. Complexing agents, organic reagents containing azo dyes as color-forming groups, mineral acids and the like are preferred.

As described above, the following embodiment is also included in the analytical method of the present invention.

(3) Namely, the absorbance of sample is measured at a first measuring cell wherein neither a masking agent nor a color-forming reagent is incorporated, followed by addition to the sample of a masking agent of a specific composition or a color former and by subsequent transfer of the resultant sample to an ensuing measuring cell where absorbance measurement is made by using a measuring light of the same wavelength as used in the first measuring cell.

Specific examples of measurement contemplated under such embodiment are typified by a sample in which a copper ion and a nickel hydrate ion are present at the same time, a sample in which a nickel ion and a bismuth ion are present at the same time, and a sample in which a nickel hydrate ion and a phosphorus ion are present at the same time.

With regard to a sample in which a copper ion is contained together with a nickel hydrate ion, absorbance A is measured by color formation of both of the ions at a first measuring cell, followed by addition of a masking agent suited for the copper ion and by subsequent transfer of the resulting sample to an ensuing measuring cell where absorbance B is measured by color formation of the nickel hydrate ion so that the copper ion is quantitatively determined from the difference between absorbances A and B.

With further regard to a sample in which a nickel hydrate ion and a bismuth ion are present at the same time, absorbance C is measured by color formation of the nickel hydrate ion at a first measuring cell, followed by addition of a color former suited for the bismuth ion and by subsequent transport of the resulting sample to an ensuing measuring cell where absorbance D is measured by color formation of both ions so that the bismuth ion is quantitatively determined from the difference between absorbances C and D.

Thiourea and so on may be suitably used as masking agents or color formers for copper.

Absorbance measurement of a sample in which a nickel hydrate ion is present along with a phosphorus ion can be accomplished in a manner similar to that of the nickel hydrate ion and bismuth ion-containing sample.

The following embodiment is also included, as stated hereinabove, in the analytical method of the present invention.

(4) Namely, the absorbance of a sample is measured at a first measuring cell wherein a color-forming reagent is incorporated, followed by addition to the sample of a masking agent of a specific composition or a color former and by subsequent transfer of the resultant sample to an ensuing measuring cell where absorbance measurement is made by using a measuring light of the same wavelength as used in the first measuring cell.

Specific examples of measurement intended to be made in this embodiment include a sample in which a cobalt ion and an iron ion are present at the same time, and a sample in which an iron ion and a copper ion are present at the same time.

Accordingly, a sample in which a cobalt ion is present together with an iron ion, absorbance E is measured by color formation of both of the ions at a first measuring cell, followed by addition of a masking agent suited for the iron ion and by subsequent transfer of the resulting sample to an ensuing measuring cell where absorbance F is measured by color formation of the cobalt ion. From absorbance F, the cobalt ion is quantitatively determinable. Quantitative determination can be made for the iron ion from the difference between absorbances E and F.

Color formers for use in both the cobalt ion and the iron ion are chosen from an aqueous solution of 5-Br-PSAA (2-(5-bromo-2-pyridyl)azo-5-(N-n-propyl-N-(3-sulfopuropyl)amino)-aniline sodium salt) and so on. A mixture of hydrochloric acid-sodium dihydrogen phosphate-hydrogen peroxide can be used as a masking agent for the iron ion.

Concerning a sample in which a copper ion and an iron ion are present at the same time, absorbance G is measured by color formation of the iron ion at a first measuring cell where a color former is incorporated, followed by addition of a color former suited for the copper ion and by subsequent transport of the resulting sample to an ensuing measuring cell where absorbance H is measured by color formation of both ions. Thus, the iron ion is quantitatively determined from absorbance G. Quantitative determination is made of the copper ion from the difference between absorbances G and H.

Aqueous phenanthroline can be used as a color former for the iron ion, and a sodium solution of basocuproine sulfonate can be used as a color former for the copper ion.

In an additional embodiment (5), the present invention provides an apparatus for simultaneously analyzing a plurality of components contained in one sample by means of continuous flow analysis, which apparatus comprises: a measuring channel in which a sample inlet, a reagent addition pipe, a reaction tube and an absorbance meter are held in integrally communicated relation to one another; and a plurality of measuring cells mounted on the absorbance meter, the measuring cells being connected in tandem so as to maintain therebetween a predetermined passageway with which is coupled a conduit arranged to add a color former and/or a masking agent, a starting sample being measured in respect of its absorbance every time the same is caused to flow through each of the measuring cells.

The following embodiment is included in the analytical apparatus of the present invention.

(6) Namely, a plurality of measuring cells are disposed on a path of irradiation of a measuring light emitted out of the absorbance meter, and a starting sample is measured in respect of its absorbance by use of the measuring light of one and the same wavelength every time the sample is caused to flow through each of the measuring cells.

In accordance with the analytical apparatus of the continuous flow type mentioned above, a plurality of color-forming components can be quantitatively determined with use of a sole absorbance meter.

Figure 1:
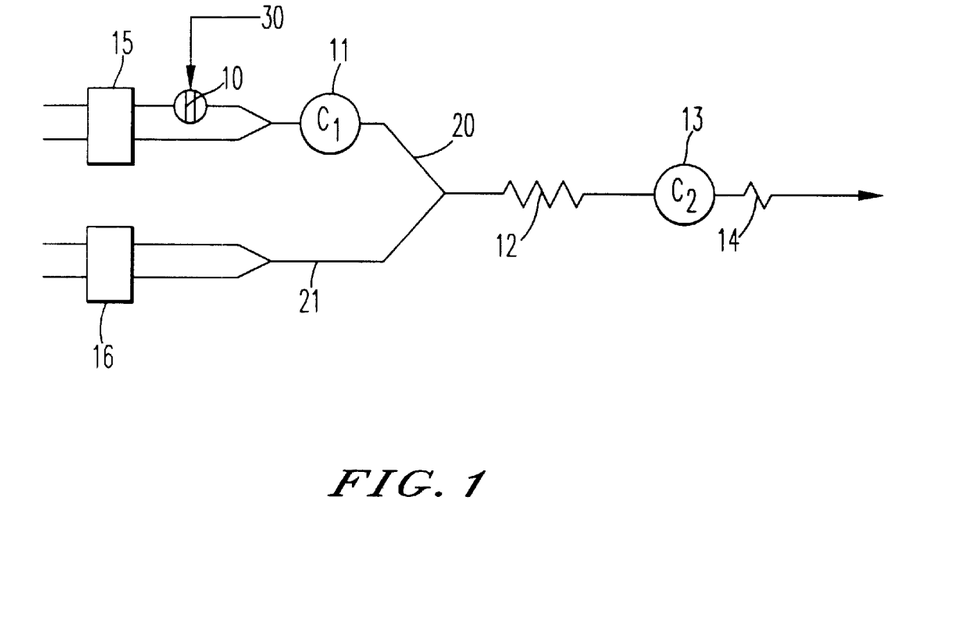
FIG. 1 is a diagrammatic illustration showing one form of a measuring system for use in the simultaneous analytical method according to the present invention.

FIG. 1 illustrates one preferred form of the measuring system for use in the analytical method according to the present invention. In FIG. 1, 10 is a sample inlet, 11 is a first measuring cell on an absorbance meter, 12 is a reaction tube, 13 is a second measuring cell on the absorbance meter, 14 is a back pressure cell to gain adjusted flow pressure, and 15 is a fluid supply pump. These parts are held in integrally communicated relation to one another by means of a measuring channel 20. Between the first measuring cell 11 and the reaction tube 12 is connected an additive supply passage 21 to which a liquid supply pump 16 is linked. The first and second measuring cells 11 and 13 are mounted on the sole absorbance meter.

(A) Measurement Example using Masking Agent

The measuring system shown in FIG. 1 is constructed based on continuous flow analysis in which a liquid sample 30 is transported through the measuring channel 20 to the absorbance meter wherein color-forming components contained in the liquid sample 30 are identified by measurement of the absorbances of such components. Employed here are a plurality of measuring cells 11 and 13 through which the liquid sample 30 is caused to flow in turn. A liquid sample 30 in which its color-forming components are not masked is conveyed with the use of a carrier liquid to the first measuring cell 11 where measurement is made for absorbance A of the liquid sample 30. To the liquid sample 30 having passed through the first measuring cell 11 is added a masking agent containing a specific ingredient, and the resulting liquid sample is thereafter transferred to the reaction tube 12. This reaction tube is of a coiled formation for ample reaction time; Applicants believe that a reaction of the liquid sample with the masking agent proceeds during traveling of the liquid sample 30 through the reaction tube 12. The liquid sample 30 masked with the specific ingredient as a result of traveling through the reaction tube 12 is introduced via the measuring channel 20 to the second measuring cell 13 on the absorbance meter where absorbance B of the masked liquid sample 30 by use of a measuring light of the same wavelength as used in the first measuring cell 11. From absorbance B and from the difference between absorbances A and B, the masked component and the component put in color-formed condition together with the former, can be analyzed or otherwise identified at the same time.

Although two measuring cells are illustrated in FIG. 1, a certain sole absorbance meter is used which is provided with measuring cells in the same number as that of components to be analyzed. In this instance, all components intended to be determined can be simultaneously identified by repeating component masking and absorbance measurement of the masked component with respect to each such component.

Specific measurements based on the above measuring system are given below. (1) By use of a liquid sample containing a copper ion and a nickel hydrate ion (an electrolytic copper liquid) and also by use of a light wavelength of 720 nm as a measuring wavelength showing absorptions of both of these ions, a selected amount of the liquid sample in which no masking agent is added is stored in the sample inlet 10 and then transported along with a dilute sulfuric acid solution as a carrier liquid to the first measuring cell 11 where measurement is made for absorbance A induced from two hydrate ions of copper and nickel.

To the liquid sample having passed through the first measuring cell 11 is subsequently added thiourea via the passage 21, and the resulting liquid sample is transferred to the reaction tube 12. During flowing of the liquid sample through the reaction tube 12, a copper complex is formed to thereby mask the copper ion. The resulting liquid sample is then put into the second measuring cell 13 where measurement is made for absorbance B induced from the nickel hydrate ion. Quantitative determination is done for nickel from absorbance B and for copper from the difference between absorbances A and B. Here, because the liquid sample gets diluted upon addition of thiourea while it moves from the first measuring cell to the second equivalent, this ratio of dilution may be decided in advance with use of a certain standard solution. From the absorbance produced at the second measuring cell, the extent required for nickel to take part in the absorbance obtained at the first measuring cell (absorbance B×dilution ratio) may be counted which is then substrated from the absorbance of the first cell so that the absorbance of copper at the first measuring cell can be decided as represented by the following formula $$[Cu] = A - tB$$

where [Cu] is the absorbance of copper, A and B are the absorbances defined above, and t is the dilution coefficient (dilution ratio); t=D1/D2 in which D1 is the absorbance of nickel at the first measuring cell, and D2 is the absorbance of nickel at the second measuring cell. (2) Concerning a liquid sample containing an iron ion and a cobalt ion (an electrolytic zinc liquid or the like), use may be made of a measuring light of wavelength of 580 nm, a dilute mineral acid solution as a carrier liquid, 5-Br-PSAA as a color former and a mixture of phosphoric acid and hydrogen peroxide as a masking agent. The iron and cobalt ions can be quantitatively determined at the same time in the same manner as in the case noted as (1) above.

(B) Measurement Example Using Color Former

In the measuring system shown in FIG. 1, a liquid sample 30, in which no color-forming reagent is added, is conveyed along with a carrier liquid to the first measuring cell 11 where measurement is made for absorbance C of the liquid sample 30. To the liquid sample 30 having passed through the first measuring cell 11 is added a color former containing a specific ingredient via the passage 21, and the resulting liquid sample is thereafter transferred to the reaction tube 12. A reaction of the liquid sample with the color former is promoted during traveling of the liquid sample 30 through the reaction tube 12. The liquid sample 30 color-formed with the specific ingredient is introduced via the measuring channel 20 to the second measuring cell 13 on the absorbance meter where absorbance D of the liquid sample 30 by use of a measuring light of the same wavelength as used in the first measuring cell 11. From absorbance C and from the difference between absorbances C and D, the specified component and the component put in color-formed condition can be analyzed or otherwise identified at the same time.

In the same manner as noted in item (A) above, a certain sole absorbance meter is used which is provided with measuring cells in the same number as that of components to be identified. In such case, all components intended to be determined can be simultaneously analyzed by incorporating color-forming reagents in turn in the associated liquid sample and then introducing the latter to ensuing measuring cells and by repeating absorbance measurements of the color-formed components.

Specific Measurements Based on the Above Measuring System are Given Below.

Using a liquid sample containing a nickel hydrate ion and a bismuth ion (an electrolytic copper liquid) and also using a light with a wavelength of 390 nm as a measuring wavelength showing absorptions of both of these ions, a selected amount of the liquid sample in which no color-forming reagent is added is stored in the sample inlet 10 and then transported along with a dilute sulfuric acid solution as a carrier liquid to the first measuring cell 11 where measurement is made for absorbance X induced from the nickel hydrate ion.

To the liquid sample having passed through the first measuring cell 11 is subsequently added thiourea applied as a color former for the bismuth ion via the additive addition passage 21, and the resulting liquid sample is transferred to the reaction tube 12. During flowing of the liquid sample through the reaction tube 12, bismuth and thiourea are reacted to cause color formation. The resulting liquid sample is then transferred into the second measuring cell 13 where measurement is made for absorbance Y induced from the nickel hydrate ion and the bismuth ion. Quantitative determination is done for nickel from absorbance X and for bismuth from the difference between absorbances X and Y.

(C) Measurement Apparatus

Figure 2:
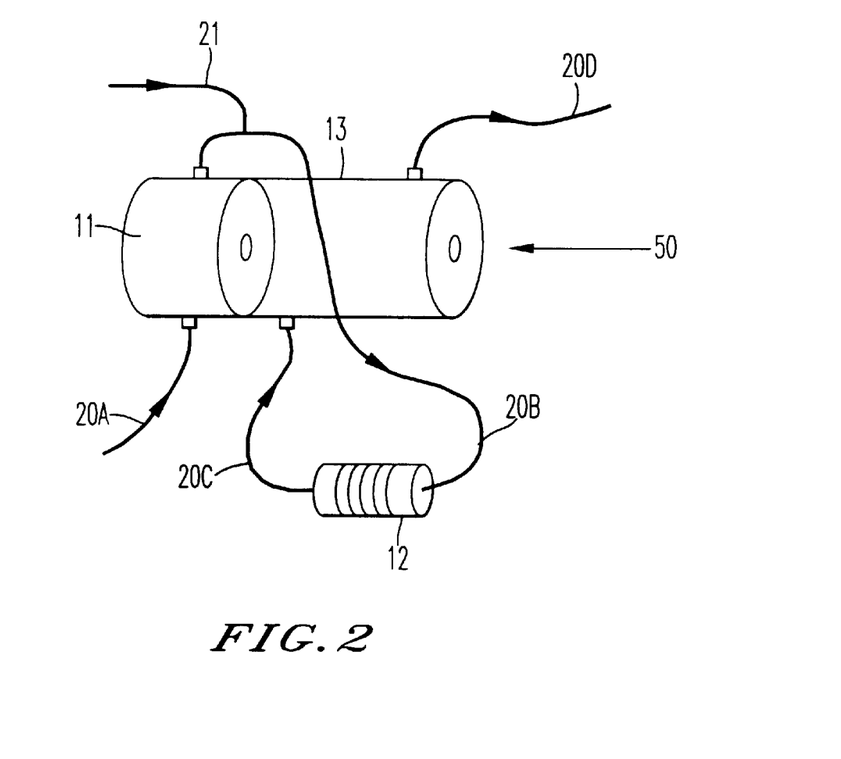
FIG. 2 schematically illustrates the positioning of measuring cells in the simultaneous analytical method of the invention.

One preferred form of the analytical apparatus according to the present invention is illustrated in FIG. 1 and FIG. 2.

As better seen in FIG. 1, the apparatus of the invention is of a structure enabling continuous flow analysis and comprising a measuring channel in which a sample inlet section 10, a reagent inlet section, a reaction section and an absorbance meter are brought into integrally communicated relation to one another. A plurality of measuring cells mounted on the absorbance meter (not shown), a first measuring cell 11 and a second measuring cell 13, are connected in tandem on a path of irradiation of a measuring light 50 emitted from the absorbance meter as shown in FIG. 2. To the first measuring cell 11 are linked a liquid sample supply pipe 20a and a pipe 20b extending to a reaction tube 12, and an additive supply passage 21 is united with the pipe 20b. To the second measuring cell 13 are linked a pipe 20c connected with the reaction tube 12 and a pipe 20d extending to a back pressure coil 14.

The reaction tube 12 of sufficient length is located between the first measuring cell 11 and the second measuring cell 13. When a liquid sample is caused to flow into the first measuring cell 11 with the aid of a carrier fluid, the second measuring cell 13 is still left empty. Thus, the measuring light 50 transmits through the second measuring cell 13, thus irradiating the first measuring cell 11 where the liquid sample is measured in respect of its absorbance.

Subsequently, the liquid sample is allowed to pass through the first measuring cell 11 and, after incorporation with an additive such as a masking agent or a color former from the passage 21, is transferred to the reaction tube 12 and then introduced into the second measuring cell 13. Upon entry into the second measuring cell 13, the liquid sample is irradiated with a light of the same wavelength as used in the first measuring cell so that measurement is made for absorbance of the liquid sample.

The following examples are provided to further illustrate the present invention. Such examples are related to those specimens composed of two color-forming components. It is to be noted, however, that even in the case of a specimen containing three or more color-forming components, measurement can be satisfactorily done with reliance upon the practices set forth hereinbelow. Further, the following examples are also presented in the Priority Document Hei 8-282323, filed under the Paris Convention on Oct. 24, 1996, which is incorporated herein by reference.

EXAMPLES

Example 1 (Cu and Ni)

Using of the apparatus of continuous flow analysis provided with the measuring system of FIG. 1 and FIG. 2 (inner diameter of piping: 1 mm, sole absorbance meter: with two measuring cells), a sulfuric acid solution of 2M in concentration was allowed to flow as a carrier fluid and in a flow rate of 4 ml/min through a measuring channel 20, and a copper- and nickel-containing liquid sample (an electrolytic copper fluid, acidified with 2M sulfric acid) was introduced in an amount of 70 μl into the measuring system. The liquid sample was irradiated with a measuring light of wavelength of 720 nm in a first measuring cell 11 to thereby measure absorbance A. To the liquid sample having passed through the first cell 11 was added thiourea of 0.75M in concentration in a flow rate of 2.5 ml/min via and from a passage 21, and the resulting liquid sample was allowed to run into a reaction tube 12 of 5 m in length and to then introduce in a second measuring cell 13 where absorbance B was measured upon irradiation of the liquid sample with a measuring light of a 720 nm wavelength as used in the first cell 11. Absorbance A is the sum T1 (Cu+Ni) of an absorbance of copper and an absorbance of nickel, whereas absorbance B is an absorbance T2 (Ni) of nickel alone.

Figure 3:
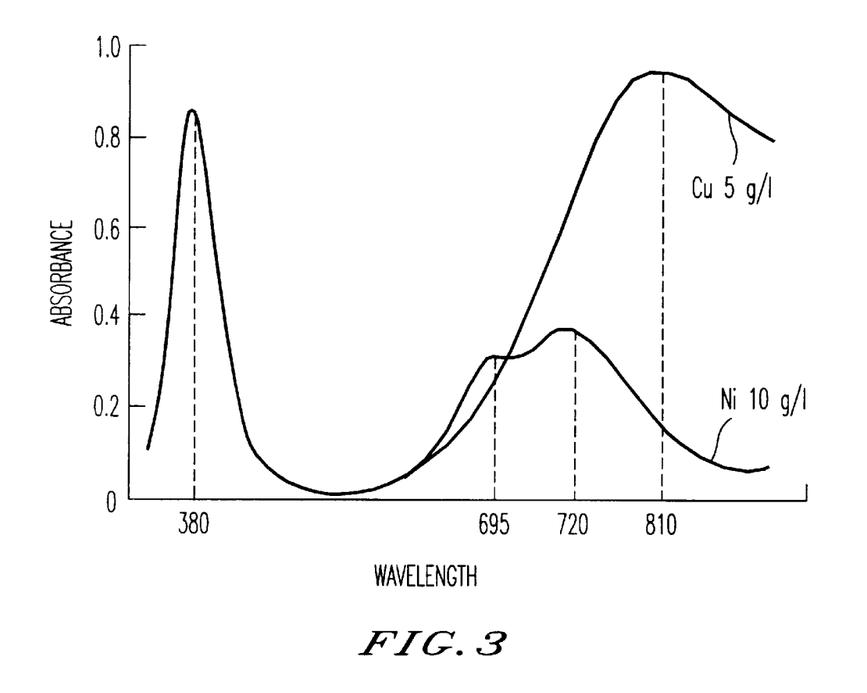
FIG. 3 shows the absorbance versus wavelength resulting from Example 1 using the simultaneous analytical method of the present invention.

During flowing from the first cell to the second cell, the liquid sample becomes diluted through association with or diffusion by the reagent added with the result that the ratio (D) of dilution produced between both of the cells is determined with the use of a standard solution of nickel, wherein D is defined by an absorbance of nickel in the first cell/an absorbance of nickel in the second cell. From the absorbance found in the second cell, the extent required for nickel to participate in the absorbance found in the first cell is computed which is then subtracted from the first cell. Thus, the absorbance of copper in the first cell is determinable as (T1(Cu)=T1(Cu+Ni)–D×T2(Ni)). The absorbances of copper and of nickel thus obtained are shown in FIG. 3.

As is clear from Table 1, the results accruing from the analytical method of the present invention are favorably comparable to those arising from a titration method (copper: iodine titration method, nickel: EDTA titration method) of the prior art and from an ICP method of the prior art. The analytical method of the invention has now been found to exhibit great precision and high accuracy as in the titration method. EDTA denotes ethylenediaminetetraacitic acid; while ICP denotes Inductively Coupled Plasma-atomic emission spectrometry.

TABLE 1

(unit: g/l):

| Sample No. | Inventive Method | | Prior art method 1 (titration method) | | Prior art method 2 (ICP method) | |
|---|---|---|---|---|---|---|
| | Cu | Ni | Cu | Ni | Cu | Ni |
| 1 | 46.5 | 16.3 | 46.1 | 15.9 | 47.0 | 16.5 |
| 2 | 44.2 | 18.6 | 43.9 | 18.7 | 44.8 | 18.9 |
| 3 | 50.1 | 8.3 | 51.0 | 7.2 | 50.5 | 9.1 |

Example 2 (Co and Fe)

Using the same apparatus as used in Example 1, an ammonium acetate solution of 1M concentration was allowed to flow as a carrier fluid with a flow rate of 2 ml/min through a measuring channel 20, and a cobalt- and iron (divalent)-containing liquid sample (an electrolytic zinc fluid, acidified with 2M sulfuric acid) was introduced in an amount of 60 µl into the measuring system. The liquid sample was associated with an aqueous solution (1ml/min) of 5-Br-PSAA of $2 \times 10^{-3}$ concentration and then transferred to a reactive coil (inner diameter of piping: 1 mm, length: 3 m, heating: 120° C.) where a PSAA complex of cobalt and iron was formed, followed by association with a flow of 1 ml/min of 2M sulfuric acid. The resultant liquid sample was irradiated with a light of wavelength of 580 nm in a first measuring cell 11 to thereby measure absorbance A. To the liquid sample having passed through the first cell 11 was added a mixture of 0.1M hydrochloric acid; 0.05M sodium dihydrogen phosphate; 0.1% hydrogen peroxide in a flow rate of 2 ml/min via and from a passage 21, and the resulting liquid sample was allowed to run into a 5 m-long reaction tube 12 and to then introduce in a second measuring cell 13 where absorbance B was measured upon irradiation of the liquid sample with a light of a 580 nm wavelength as used in the first cell 11. Absorbance A is the sum of T1 (Co+Fe) of an absorbance of cobalt and an absorbance of iron, whereas absorbance B is an absorbance T2 (Co) of cobalt alone.

Figure 4:
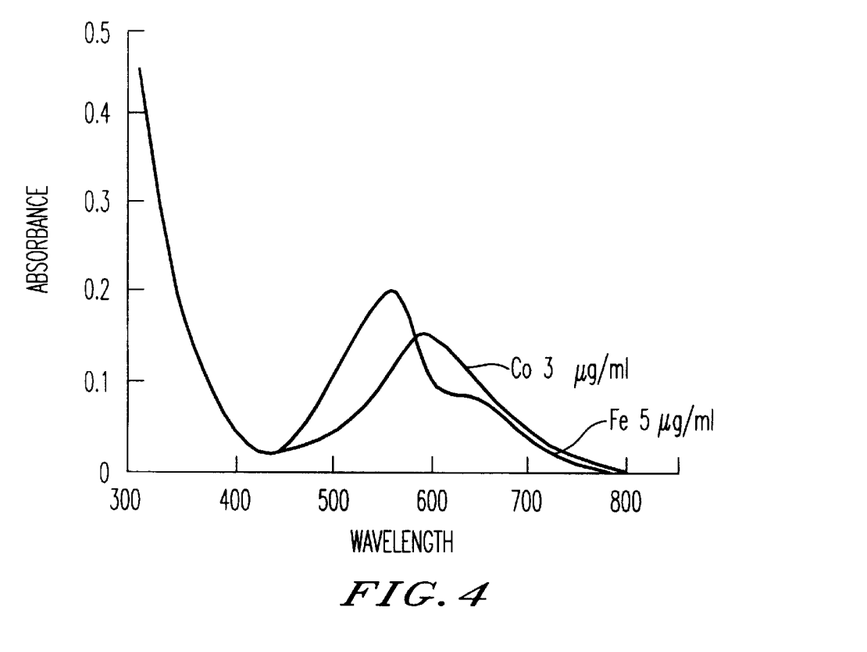
FIG. 4 shows the absorbance versus wavelength obtained in Example 2.

In going from the first cell to the second cell, the liquid sample becomes diluted through association with or diffusion by the reagent added with the result that the ratio (D) of dilutution produced between both of the cells is determined with the use of a standard solution of cobalt, wherein D is defined by an absorbance of cobalt in the first cell/an absorbance of cobalt in the second cell. From the absorbance found in the second cell, the extent required for cobalt to participate in the absorbance found in the first cell is computed which is then subtracted from the first cell. Thus, the absorbance of iron in the first cell is determinable as (T1(Fe)=T1Co+Fe)–D×T2(Co)). The absorbances of iron and of cobalt thus obtained are shown in FIG. 4.

As is evident from Table 2, the results accruing from the analytical method of the invention are favorably comparable to those arising from a measuring method (cobalt: atomic absorption method in graphite furnace, iron: ICP method) of the prior art. The analytical method of the invention has now been found to offer automatic analysis with great sensitivity and high accuracy.

TABLE 2

(unit: mg/l)

| Sample No. | Inventive method | | Prior art method | |
|---|---|---|---|---|
| | Co | Fe | Co | Fe |
| 1 | 0.5 | 2.0 | 0.3 | 2.2 |
| 2 | 0.1 | 5.6 | 0.2 | 5.9 |
| 3 | 0.4 | 13.1 | 0.3 | 13.8 |

Example 3-1 (Ni and Bi)

Using of the same apparatus as used in Example 1, a 1M sulfuric acid solution was allowed to flow as a carrier fluid with a flow rate of 2 ml/min through a measuring channel 20, and a nickel- and bismuth-containing liquid sample (an electrolytic copper fluid separated by sedimentation, acidified with 2M sulfuric acid) was introduced in an amount of 80 µl into the measuring system. The resultant liquid sample was irradiated with a light of wavelength of 390 nm in a first measuring cell 11 to thereby measure absorbance A. To the liquid sample having passed through the first cell 11 was added a 0.75M thiourea solution with a flow rate of 2 ml/min via and from an additive addition passage 21, and the resulting liquid sample was allowed to run into a 5 m-long reaction tube 12 and to then introduce in a second measuring cell 13 where absorbance B was measured upon irradiation of the liquid sample with a measuring light of a 390 nm wavelength as used in the first cell 11. Absorbance A is an absorbance T1 (Ni) of nickel alone, whereas absorbance B is the sum of T2 (Ni+Bi) of an absorbance of nickel and an absorbance of bismuth.

Figure 5:
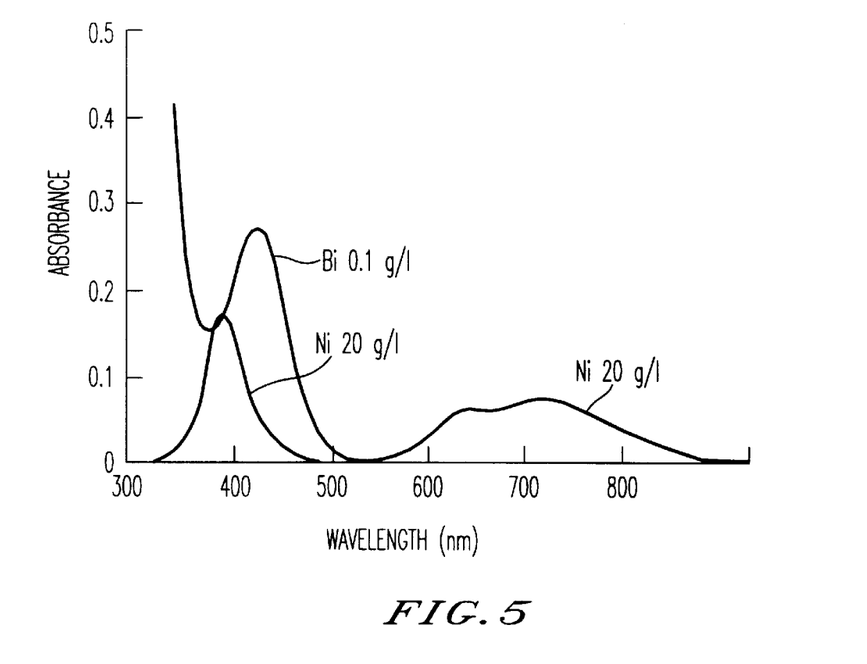
FIG. 5 shows the absorbance versus wavelength obtained in Example 3-1.

In going from the first cell to the second cell, the liquid sample becomes diluted through association with or diffusion by the reagent added with the result that the ratio (D) of dilution produced between both of the cells is determined with the use of a standard solution of nickel, wherein D is defined by an absorbance of nickel in the first cell/an absorbance of nickel in the second cell. From the absorbance found in the second cell, the extent required for nickel to participate in the absorbance found in the first cell is computed which is then subtracted from the first cell. Thus, the absorbance of bismuth in the first cell is determined as (T2(Bi)=T2(Ni+Bi)−D×T1(Ni)). The absorbances of bismuth and of nickel thus obtained are shown in FIG. 5.

As is apparent from Table 3, the results accruing from the analytical method of the invention are favorably comparable to those arising from a measuring method (nickel: EDTA titration method, bismuth: atomic absorption method) of the prior art. The analytical method of the invention has now been found to offer automatic analysis with great sensitivity and high accuracy.

TABLE 3

| Sample | Inventive method | | Prior art method | |
| --- | --- | --- | --- | --- |
| No. | Ni | Bi | Ni | Bi |
| 1 | 16.3 | 0.13 | 16.9 | 0.15 |
| 2 | 18.6 | 0.17 | 19.3 | 0.14 |
| 3 | 8.3 | 0.08 | 9.1 | 0.09 |

(unit: g/l)

Example 3-2 (Ni and P)

Using the same apparatus as used in Example 1, a 1M sulfuric acid solution was allowed to flow as a carrier fluid and with a flow rate of 2 ml/min through a measuring channel 20, and a nickel- and phosphorus-containing liquid sample (a nickel plating fluid, slightly acidified) was introduced in an amount of 200 μl into the measuring system. The resultant liquid sample was irradiated with a light of wavelength of 390 nm in a first measuring cell 11 to thereby measure absorbance A. To the liquid sample having passed through the first cell 11 was added a mixture of 0.01M ammonium molybdate; 0.075M sulfuric acid at a flow rate of 2 ml/min via and from an additive passage 21, and the resulting liquid sample was allowed to run into a 5 m-long reaction tube 12 and to then introduce in a second measuring cell 13 where absorbance B was measured upon irradiation of the liquid sample with a measuring light of a 390 nm wavelength as used in the first cell 11.

Absorbance A is an absorbance T1 (Ni) of nickel alone, whereas absorbance B is the sum of T2 (Ni+P) of an absorbance of nickel and an absorbance of phosphorus.

Figure 6:
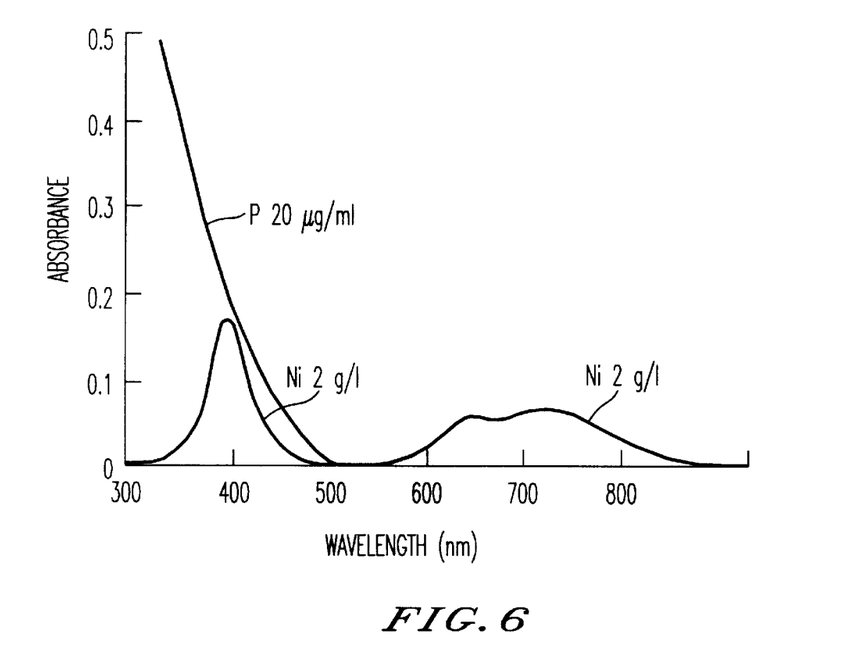
FIG. 6 shows the absorbance versus wavelength obtained in Example 3-2.

In going from the first cell to the second cell, the liquid sample becomes diluted through association with or diffusion by the reagent added with the result that the ratio (D) of dilution produced between both of the cells is determined with the use of a standard solution of nickel, wherein D is defined by an absorbance of nickel in the first cell/an absorbance of nickel in the second cell. From the absorbance found in the second cell, the extent required for nickel to participate in the absorbance found in the first cell is computed which is then subtracted from the first cell. Thus, the absorbance of phosphorus in the first cell is determined as (T2(P)=T2(Ni+P)−D×T1(Ni)). The absorbances of nickel and phosphorus thus obtained are shown in FIG. 6.

As evidenced by Table 4, the results accruing from the analytical method of the invention have been found to be favorably comparable to those arising from a measuring method (nickel: EDTA titration method, phosphorus: absorption spectrometry by yellow molybdenum) of the prior art. The analytical method of the invention can provide automatic analysis with great sensitivity and high accuracy.

TABLE 4

| Sample | Inventive method | | Prior art method | |
| --- | --- | --- | --- | --- |
| No. | Ni | P | Ni | P |
| 1 | 150 | 0.001 | 148 | <0.001 |
| 2 | 148 | 0.002 | 149 | 0.001 |
| 3 | 125 | 0.003 | 1128 | 0.004 |

(unit: g/l)

Example 4 (Fe and Cu)

By the use of the same apparatus as used in Example 1, a mixture of a 1M ammonium acetate solution and a 0.5M hydroxylamine hydrochloride salt was allowed to flow as a carrier fluid, at a flow rate of 2 ml/min through a measuring channel 20, and an iron- and copper-containing liquid sample (a zinc electrolyte, acidified with 2M sulfuric acid) was introduced in an amount of 100 μl into the measuring system. The liquid sample was admixed with an aqueous solution (1 ml/min) of $2\times10^{-3}$ M 1,10-phenanthroline and then transferred to a reactive coil (inner diameter of piping: 1 mm, length: 3 m) where an iron-phenanthroline complex was formed. The resultant liquid sample was irradiated with a light having a wavelength of 520 nm in a first measuring cell 11 to thereby measure absorbance A. To the liquid sample having passed through the first cell 11 was added a sodium solution of $2\times10^{-3}$ M basocuproin sulfonate at a flow rate of 1 ml/min via and from a passage 21, and the resulting liquid sample was allowed to run into a 5 m-long reaction tube 12 and to then introduce in a second measuring cell 13 where absorbance B was measured upon irradiation of the liquid sample with a light of a 520 nm wavelength as used in the first cell 11. Absorbance A is an absorbance T1 (Fe) of iron, and absorbance B is the sum T2 (Fe+Cu) of an absorbance of iron and an absorbance of copper.

Figure 7:
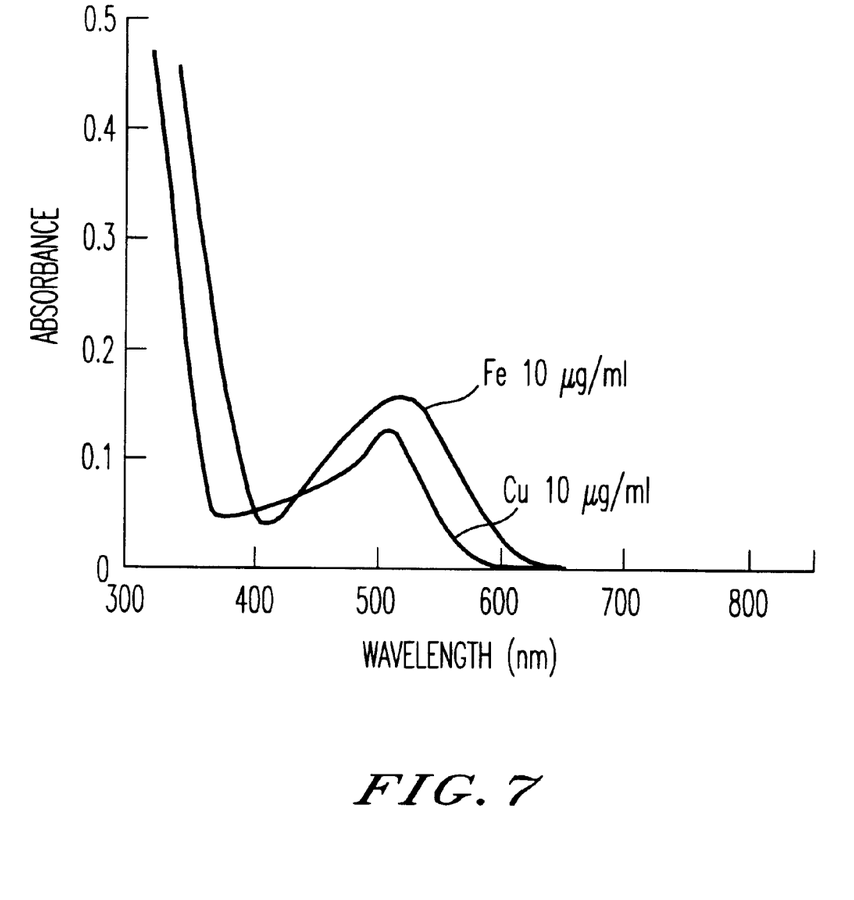
FIG. 7 shows the absorbance versus wavelength obtained in Example 4.

In going from the first cell to the second cell, the liquid sample becomes diluted through association with or diffusion by the reagent added with the result that the ratio (D) of dilution produced between both cells is determined with the use of a standard solution of iron, wherein D is defined by an absorbance of iron in the first cell/an absorbance of iron in the second cell. From the absorbance found in the second cell, the extent required for iron to participate in the absorbance found in the first cell is computed which is then subtracted from the first cell. Thus, the absorbance of copper in the first cell is determinable as (T2(Cu)T2(Fe−Cu)−D×T1(Cu)). The absorbances of iron and of copper thus obtained are shown in FIG. 7.

As is evident from Table 5, the results accruing from the analytical method of the invention are favorably comparable to those arising from a measuring method (ICP method) of the prior art. The analytical method of the invention has now been found to offer automatic analysis with great sensitivity and high accuracy.

TABLE 5

| Sample | Inventive method (unit: mg/l) | | Prior art method | |
|---|---|---|---|---|
| No. | Fe | Cu | Fe | Cu |
| 1 | 2.0 | 0.1 | 2.2 | 0.2 |
| 2 | 5.6 | 0.2 | 5.9 | 0.2 |
| 3 | 13.1 | 0.3 | 13.8 | 0.3 |

In accordance with the method of continuous flow analysts of the present invention, a plurality of color-forming components contained in a sample can be analyzed or identified at one time with the use of a light of the same wavelength. Additionally, this method affords analysis with enhanced precision but with no need for varied wavelength for measurement. Also advantageously, the method is easy to operate and capable of continuous measurement with possible analysis of a large number of samples for a shorter period of time.

Meanwhile, the analytical apparatus of the invention is simple in construction due to a plurality of measuring cells mounted on a sole absorbance meter and hence is convenient to practice in a wide range of applications.

What is claimed is:

1. A method of simultaneously analyzing a plurality of components by continuous flow analysis, which comprises:

(a) selecting a sample containing at least two components to be analyzed;

(b) introducing said sample into the first of at least two measuring cells connected in series;

(c) irradiating said sample with light which generates a wavelength corresponding to absorption bands of the components in said sample;

(d) measuring the absorbance of said sample;

(e) circulating the irradiated sample through a channel toward a second measuring cell;

(f) adding a reagent to said irradiated sample while in said channel, said reagent causing a change in the absorbance of at least one of said components;

(g) measuring the absorbance of the sample while in said second measuring cell;

(h) comparing the absorbances of each measurement to identify the components in said sample.

2. A method according to claim 1 wherein said reagent comprises at least one of a color former or a masking agent.

3. A method according to claim 2 wherein the sample measured in said first cell contains a color former and the added reagent is a masking agent.

4. A method according to claim 2 wherein the sample measured in said first cell is free of a color former or a masking agent, and the absorbance in each cell is measured using light of the same wavelength.

5. The method according to claim 1, wherein said light generates a wavelength selected from the group consisting of 750 nm, 580 nm, 520 nm and 390 nm.

6. The method according to claim 1, wherein said light generates a wavelength corresponding to absorption bands characteristic of copper hydrate ion, nickel hydrate ion, cobalt ion complex with 2-(5-bromo-2-pyridyl)-azo-5-(N-n-propyl-N-(-3-sulfopuropyl)amino)-aniline sodium salt, iron ion, iron ion complex with ortho-phenanthroline, copper ion complex with basocuproine sulfonate, thiourea complex of bismuth or molybdic acid complex of ortho-phosphoric acid.

* * * * *